United States Patent
Schmitt et al.

(10) Patent No.: US 6,187,033 B1
(45) Date of Patent: Feb. 13, 2001

(54) AORTIC ARCH PROSTHETIC GRAFT

(75) Inventors: Peter J. Schmitt, Garnerville, NY (US); Klaus Heck, Kinnelon; James Rudnick, Waldwick, both of NJ (US)

(73) Assignee: Meadox Medicals, Inc., Oakland, NJ (US)

(*) Notice: Under 35 U.S.C. 154(b), the term of this patent shall be extended for 0 days.

(21) Appl. No.: 08/923,298

(22) Filed: Sep. 4, 1997

(51) Int. Cl.$^7$ .................................................. A61F 2/06
(52) U.S. Cl. ................................. 623/1; 623/12
(58) Field of Search ................. 623/1, 12; 606/194, 606/195; 600/36

(56) References Cited

U.S. PATENT DOCUMENTS

| | | |
|---|---|---|
| 2,127,903 | 8/1938 | Bowen . |
| 3,108,357 | * 10/1963 | Liebig ........................ 623/1 |
| 4,309,776 | 1/1982 | Berguer . |
| 4,313,231 | 2/1982 | Koyamada . |
| 4,497,074 | 2/1985 | Rey et al. . |
| 4,501,263 | 2/1985 | Harbuck . |
| 4,503,568 | 3/1985 | Madras . |
| 4,512,761 | 4/1985 | Raible . |
| 4,546,499 | 10/1985 | Possis et al. . |
| 4,601,718 | 7/1986 | Possis et al. . |
| 4,668,545 | 5/1987 | Lowe . |
| 4,795,465 | 1/1989 | Marten . |
| 4,816,028 | * 3/1989 | Kapadia et al. .................. 623/1 |
| 4,923,724 | 5/1990 | Day et al. . |
| 4,994,071 | 2/1991 | MacGregor . |
| 5,127,919 | * 7/1992 | Ibrahim et al. .................. 623/1 |
| 5,156,619 | 10/1992 | Ehrenfeld . |
| 5,178,634 | 1/1993 | Martinez . |
| 5,197,976 | 3/1993 | Herweck et al. . |
| 5,282,848 | * 2/1994 | Schmitt ........................ 623/12 |
| 5,314,468 | 5/1994 | Martinez . |
| 5,456,712 | 10/1995 | Maginot . |
| 5,489,295 | 2/1996 | Piplani et al. . |
| 5,575,817 | * 11/1996 | Martin ........................ 623/1 |
| 5,584,803 | 12/1996 | Stevens et al. . |
| 5,591,228 | 1/1997 | Edoga . |
| 5,617,878 | 4/1997 | Taheri . |
| 5,632,763 | 5/1997 | Glastra . |
| 5,632,772 | 5/1997 | Alcime et al. . |
| 5,639,278 | 6/1997 | Dercume et al. . |
| 5,643,340 | 7/1997 | Nunokawa . |
| 5,653,743 | 8/1997 | Martin . |

FOREIGN PATENT DOCUMENTS

| | | |
|---|---|---|
| 0 269 254 | 6/1988 | (EP) . |
| 2 105 197 | 3/1983 | (GB) . |
| 692-923 | 10/1979 | (SU) . |
| 740-877 | 6/1980 | (SU) . |
| 9421197 | * 4/1994 | (WO) ........................ 623/1 |

OTHER PUBLICATIONS

Wylie, et al., "Manual of Vascular Surgery", vol. I, pp. 14–29.
"Renovascular Atherosclerosis" pp. 233–257.

* cited by examiner

Primary Examiner—Bruce E. Snow
(74) Attorney, Agent, or Firm—Hoffmann & Baron, LLP

(57) ABSTRACT

An implantable tubular textile prosthesis particularly useful in branched end-to-side anastomoses is provided. The prosthesis includes a first portion including an elongate tubular main wall which defines a fluid passageway therethrough, and a second portion including a tubular branch wall which extends laterally from the tubular main wall and which defines a fluid passageway therethrough. The tubular branch wall includes an elongate tubular extent and a contiguous flared tubular extent. The tubular branch wall is secured to the tubular main wall at the flared tubular extent to establish fluid communication between the passageways of the tubular main wall and the tubular branch wall. The flared tubular extent includes a gradual increase in diameter with respect to the tubular branch extent to provide a seamless and substantially fluid-tight transition between the tubular main wall and the tubular branch wall along the flared tubular extent.

19 Claims, 7 Drawing Sheets

AORTIC ARCH PROSTHETIC GRAFT

FIELD OF THE INVENTION

The present invention is directed generally to a vascular prosthesis which is useful in repair or replacement of a branched section of a blood vessel. More particularly, the present invention provides a textile vascular graft which is substantially fluid-tight and which is particularly useful in branched end-to-side anastomoses.

BACKGROUND OF THE INVENTION

The use of tubular textile fabrics for soft-tissue implantable prostheses is well known in the repair or replacement of damaged or diseased lumens in the body. For example, tubular devices or conduits are used to repair lumens such as in the esophagus and colon areas, and, in particular, prostheses are used in the vascular system to repair, buttress or replace a weakened section of the vessel. Such conduits are generally affixed in a specified location in the vessel by means of sutures, stents, hooks or other mechanisms which serve to secure the device in place.

Synthetic vascular grafts for the repair or replacement of blood vessels have taken a wide variety of configurations and shapes. The most common type of vascular graft is that manufactured in a generally tubular form extending along a longitudinal axis. Such tubular vascular grafts are particularly well suited for use in end-to-end anastomoses, i.e., where the damaged portion of the blood vessel is dissected and the ends of the tubular graft are connected to the cut ends of the blood vessel to span the dissected portion. These tubular grafts may also be used in end-to-side anastomoses, i.e., where the end of a graft tube is typically attached to the side of a blood vessel. Such tubular vascular grafts are also useful in percutaneous applications, where the graft is inserted percutaneously and is positioned to span a damaged or diseased portion of a blood vessel without dissection.

Various designs have been proposed in order to provide for proper suturing and proper internal blood flow with end-to-end as well as end-to-side vascular grafts. For example, U.S. Pat. No. 5,156,619 discloses a flanged end-to-side vascular graft which is provided in the form of a tubular vascular graft having a flared end portion. Such a graft is cannibalized, i.e., cut, from a conventional bifurcated graft structure which includes a main tubular section and two smaller branched tubular sections. The bifurcated graft is cut along an arcuate segment at the bifurcated arch between the bifurcated tubular sections and along the wall of the main tubular section, to provide a single tubular graft with a flanged end formed from the arcuate cut. The flanged end, however, typically requires stitching along the flanged portion, since bifurcated textile grafts of the prior art typically require suturing at the bifurcated portion in order to be blood-tight. Further, as the flanged graft in the '619 patent is constructed of only a single tube with a flange at one end, it is designed to be attached to an end of a blood vessel, and is not suitable for repair or replacement of a branched section of a blood vessel. Still further, the graft disclosed in the '619 patent is designed to extend from the blood vessel at a gradually sloping angle, and would not be appropriate for applications where an end-to-side graft is required which incorporates a branch extending substantially perpendicular to a main tubular section.

Occasionally, it is necessary to provide an end-to-side vascular graft in which the side branch portion extends substantially perpendicular from the main portion to replace a portion of a blood vessel or to be positioned within a portion of a vessel which splits into one or more branch vessels. In order to overcome the deficiencies of earlier end-to-side grafts which do not include a generally perpendicular extending branch, true end-to-side vascular grafts have been constructed with branch portions which extend generally perpendicular to the main tubular section. Such end-to-side vascular grafts have typically been constructed by suturing one tubular vascular graft to the side of a second tubular vascular graft. Such end-to-side vascular grafts are used, for example, to repair or replace a damaged or diseased portion of the aorta. In such procedures, an aortic vascular prosthesis which includes a main aortic trunk portion and arterial branch portions extending generally perpendicular to the main aortic trunk portion for the left and right carotid arteries and the subclavian artery is particularly well suited. In order to provide an aortic vascular prosthesis with three branches, a surgeon will typically suture three separate straight tubular vascular grafts to the side of a larger tubular graft. Such suturing, however, usually occurs immediately prior to or during a procedure, is labor intensive and requires extreme skill and precision in suturing, thereby introducing the potential for human error.

Prior art end-to-side vascular grafts such as the aforementioned aortic vascular prostheses have not been completely successful. In particular, the attachment of one tubular graft to the side of another tubular graft results in a sharp transition, typically with an immediate transition of 90° from the main tubular section to the branched tubular section. Additionally, such attachment results in suturing or stitching directly at the point of transition between the main tubular section and the branched tubular section. Such sharp transitioning and suturing at this transition result in poor blood flow through the transitional portion, and can lead to an undesirable thrombosis at the transition.

Alternatively, custom-made aortic vascular prostheses can be constructed. While these custom-made structures may overcome some of the aforementioned deficiencies, they are extremely expensive and time-consuming to fabricate.

Accordingly, there is a need for a vascular graft which is useful in repair or replacement of a branched section of a blood vessel which is substantially blood-tight and includes a gradual transition from the main lumen to the branched lumen, and which does not include any suturing directly at the lumen transition.

SUMMARY OF THE INVENTION

It is an object of the present invention to provide a vascular graft which is useful in the repair or replacement of a blood vessel.

It is a further object of the present invention to provide a branched vascular graft which is useful in an end-to-side anastomosis.

It is a further object to provide an end-to-side vascular graft which includes a gradual transition from the main portion to the branched portion.

It is yet a further object of the present invention to provide a branched aortic arch vascular graft which is useful in end-to-side anastomoses involving the aorta and arterial branches of the left and right carotid arteries and the subclavian artery.

In the efficient attainment of these and other objects, the present invention provides an implantable tubular textile prosthesis which includes a first portion including an elongate tubular main wall which defines a fluid passageway therethrough, and a second portion including a tubular branch wall which extends laterally from the tubular main wall and which defines a fluid passageway therethrough. The tubular branch wall includes an elongate tubular extent and a contiguous flared tubular extent. The tubular branch wall is secured to the tubular main wall at the flared tubular extent to establish fluid communication between the passageways of the tubular main wall and the tubular branch wall. The flared tubular extent incorporates a gradual increase in diameter with respect to the tubular branch extent to provide a seamless and substantially fluid-tight transition between the tubular main wall and the tubular branch wall along the flared tubular extent.

The flared tubular extent may include a textile pattern which has a plurality of warp yarns and fill yarns and incorporates a gradual change in the number of warp yarns with respect to the fill yarns. The gradual change is preferably defined by a change of no more than 3 warp yarns for every 2 fill yarns in the textile pattern.

The prosthesis of the present invention is a textile product, and is preferably constructed of textile materials such as woven materials, knitted materials, braided materials, and mixtures thereof. The textile material may be any known material, for example, polyester, polypropylene, polyethylene, polyurethane, polytetrafluoroethylene and mixtures thereof.

The tubular main wall of the prosthesis may be straight, or, more preferably, may be arched, for example, by preforming into the shape of an aorta, with the elongate tubular extent extending substantially perpendicular from the main tubular wall. The prosthesis may include a plurality of elongate tubular extents at the tubular branch portion, and preferably includes three elongate tubular extents, for anastomosis with the left, right and subclavian arteries, respectively. The plurality of elongate tubular extents may be of equal or different diameters and lengths. In particularly preferred embodiments, the plurality of elongate tubular extents are spaced along an axis with respect to the tubular main wall, and are circumferentially offset with respect to the tubular main wall. The prosthesis may further include an elongate tubular port extending laterally from the tubular main wall at a location remote from the tubular branch wall, which is particularly useful during implantation procedures.

DETAILED DESCRIPTION OF THE INVENTION

As noted, the present invention is directed to a vascular prosthesis which is useful in repair or replacement of a branched section of a blood vessel, and provides a textile vascular graft which is substantially fluid-tight and which is particularly useful in branched end-to-side anastomoses.

The prosthesis of the present invention is constructed of a textile material. Textile materials, for example textile tubular prostheses which are woven, knitted and/or braided, have gained widespread use as implantable tubular prostheses. In particular, woven or knitted textile tubular prostheses which are manufactured using tubular flat-weaving techniques are a common implant material for vascular grafts.

In tubular textile manufacturing processes, a variety of yarns are interlaced to create a tubular product. For example, a set of warp yarns is used which represents the longitudinal axis of the product being manufactured, and a fill yarn is interlaced in a transverse relation between the warp yarns. The fill yarn is continuously interlaced across the length of the warp yarns to form a tubular textile structure. Such manufacture will be discussed in more detail herein.

Figure 1:
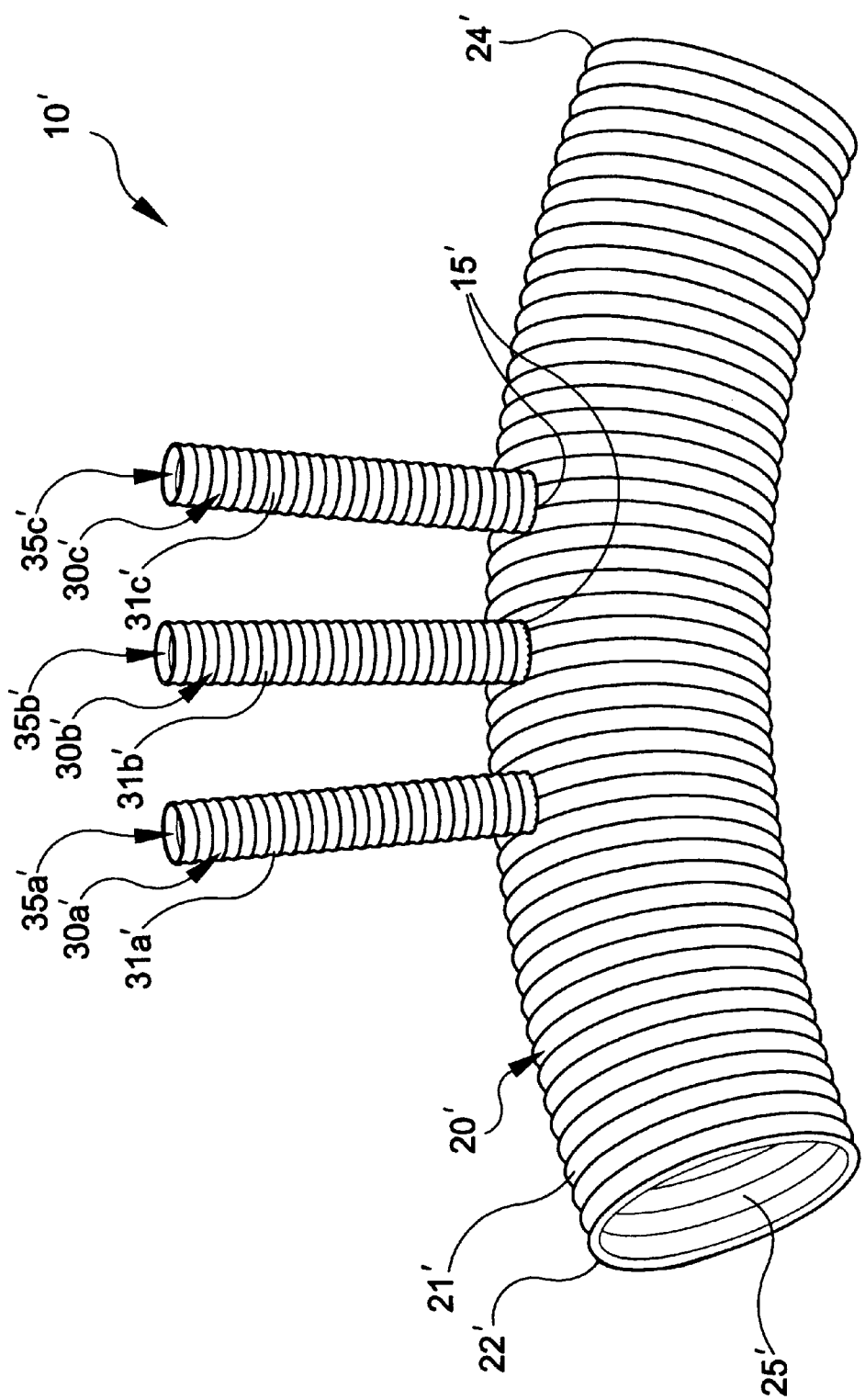
FIG. 1 is a perspective view of an aortic graft constructed in accordance with the prior art.

With specific reference to FIG. 1, a conventional aortic arch prosthesis 10' of the prior art is shown. Prosthesis 10' includes generally longitudinal tubular main portion 20' including elongate tubular main wall 21'. Tubular main portion 20' includes a first open end 22' and an opposed second open end 24', and further includes a main lumen 25' extending therethrough. Tubular branches 30a', 30b' and 30c' extend laterally from tubular main wall 21' of tubular main portion 20'. Tubular branches 30a', 30b' and 30c' include tubular branch walls 31a', 31b' and 31c', respectively, which define branch lumens 35a', 35b' and 35c', respectively. Tubular branches 30a', 30b' and 30c' are individually sutured to tubular main portion 20' at the intersection of each tubular branch wall 31a', 31b' and 31c' with tubular main wall 21' thereof by sutures 15'. As such, a path of fluid communication between main lumen 25' of tubular main portion 20' and branch lumens 35a', 35b' and 35c' of tubular branches 30a', 30b' and 30c' is established, thereby providing a passageway for blood flow therethrough. The sutures, however, are positioned directly at the transition of main tubular lumen 25' with branch lumens 35a', 35b' and 35c'.

Figure 2:
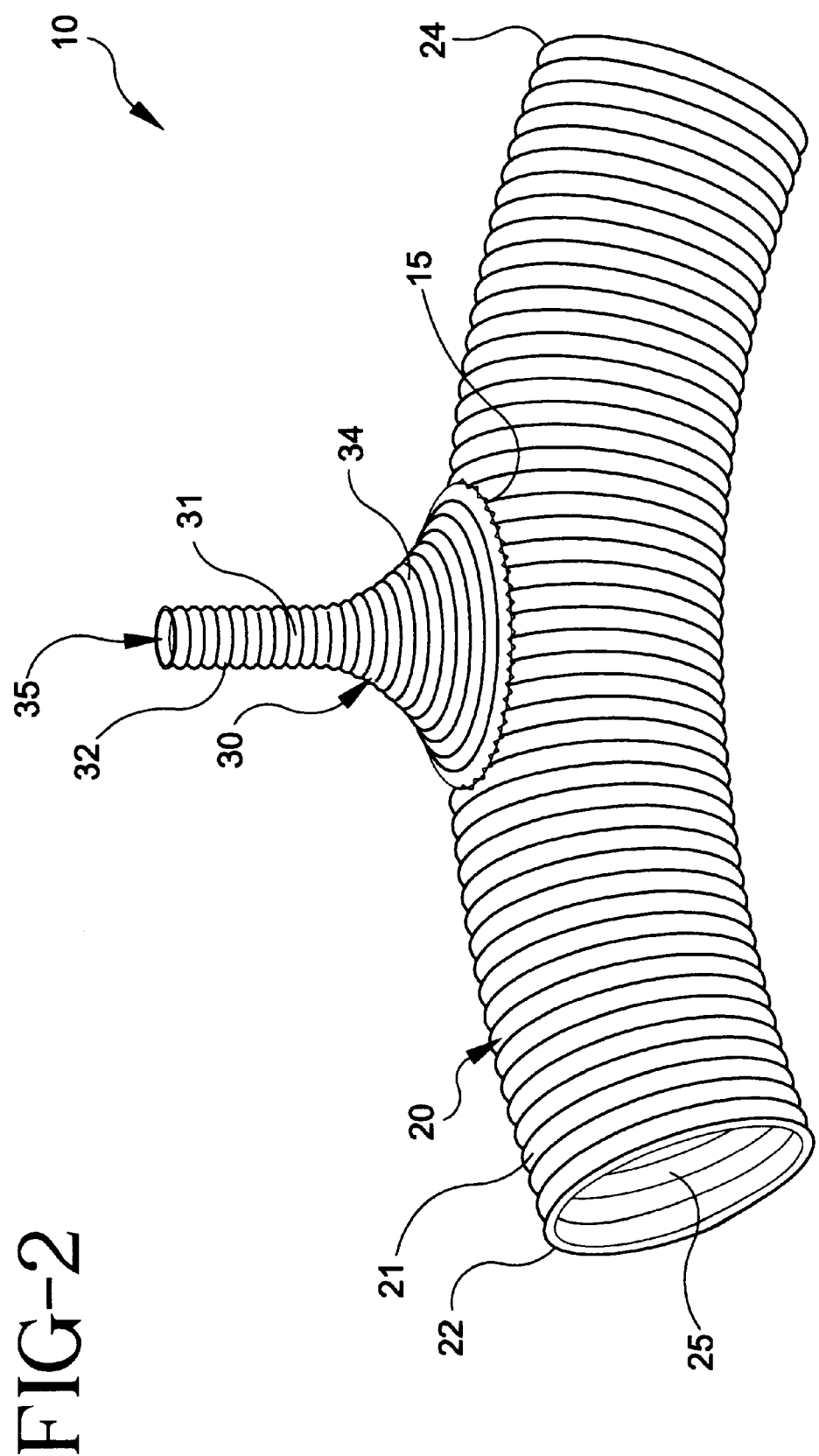
FIG. 2 is a perspective view of a textile vascular graft according to the present invention.

Referring now to FIG. 2, a branched prosthesis 10 according to the present invention is shown. Prosthesis 10 includes generally longitudinal tubular main portion 20 including elongate tubular main wall 21. Tubular main portion 20 further includes first open end 22 and opposed open end 24, with a main lumen 25 extending therethrough. Tubular main portion 20 is preferably of a generally constant internal diameter along the length thereof. In preferred embodiments, tubular main portion 20 is constructed so as to repair or replace a damaged portion of an aorta in an adult mammal. Accordingly, tubular main portion 20 includes an internal diameter appropriately sized for such use, for example, approximately 26 millimeters. Alternatively, tubular main portion 20 may be constructed with an internal diameter which varies along the length thereof.

Tubular main portion 20 may be constructed of any known textile material. For example, tubular main portion 20 may be a textile material selected from the group consisting of woven material, knitted material, braided material, and the like. Preferably, tubular main portion 20 is a woven textile material. Additionally, the textile material may include a velour inner and/or outer surface, for instance, to facilitate tissue ingrowth and cell attachment thereto.

While tubular main portion 20 is generally elongate in shape, it may be configured into any desirable shape. For example, in the preferred use as an aortic graft, tubular main portion 20 may be arched in shape to resemble the natural arch of the aorta. Such arch may be accomplished by providing tubular main wall 21 with crimps, as is known in the art. Alternatively, such arch may be provided by incorporating heat-settable material into the textile material of tubular main portion 20, which heat-settable material is capable of setting to a desired shape upon application of heat.

Prosthesis 10 further includes tubular branch 30 defined by elongate tubular branch wall 31, extending laterally from tubular main wall 21 of tubular main portion 20. Tubular branch 30 may extend laterally from tubular main wall 21 at any angle with respect thereto. Most preferably, tubular branch 30 extends substantially perpendicularly from tubular main wall 21.

As with tubular main portion 20, tubular branch 30 may also be constructed of any known textile material. For example, tubular branch 30 may be a textile material selected from the group consisting of woven material, knitted material, braided material, and the like. Preferably, tubular main portion 20 and tubular branch portion 30 are constructed of similar textile material, for instance, woven textile material.

Tubular branch wall 31 includes an elongate tubular extent 32 and a flared tubular extent 34 contiguous therewith. Additionally, tubular branch 30 includes branch lumen 35 defining a fluid passageway therethrough. Tubular branch wall 31 is of a generally constant internal diameter along the length of elongate tubular extent 32. At flared tubular extent 34, however, the internal diameter of tubular branch wall 31 gradually changes, in that it increases or flares with respect to elongate tubular extent 32.

Figure 3:
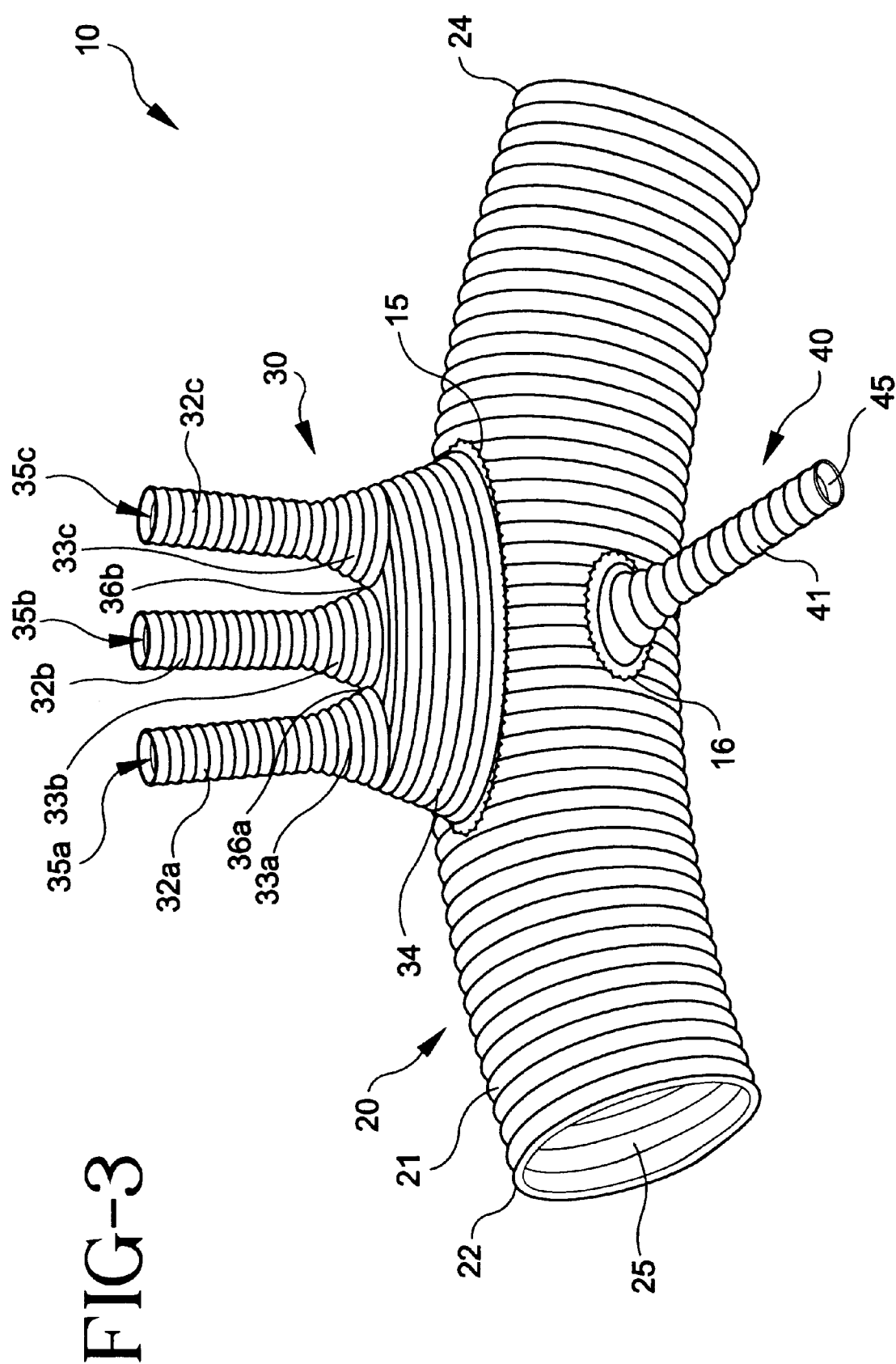
FIG. 3 is a perspective view of an aortic arch graft constructed in accordance with the preferred embodiment of the present invention.
Figure 4:
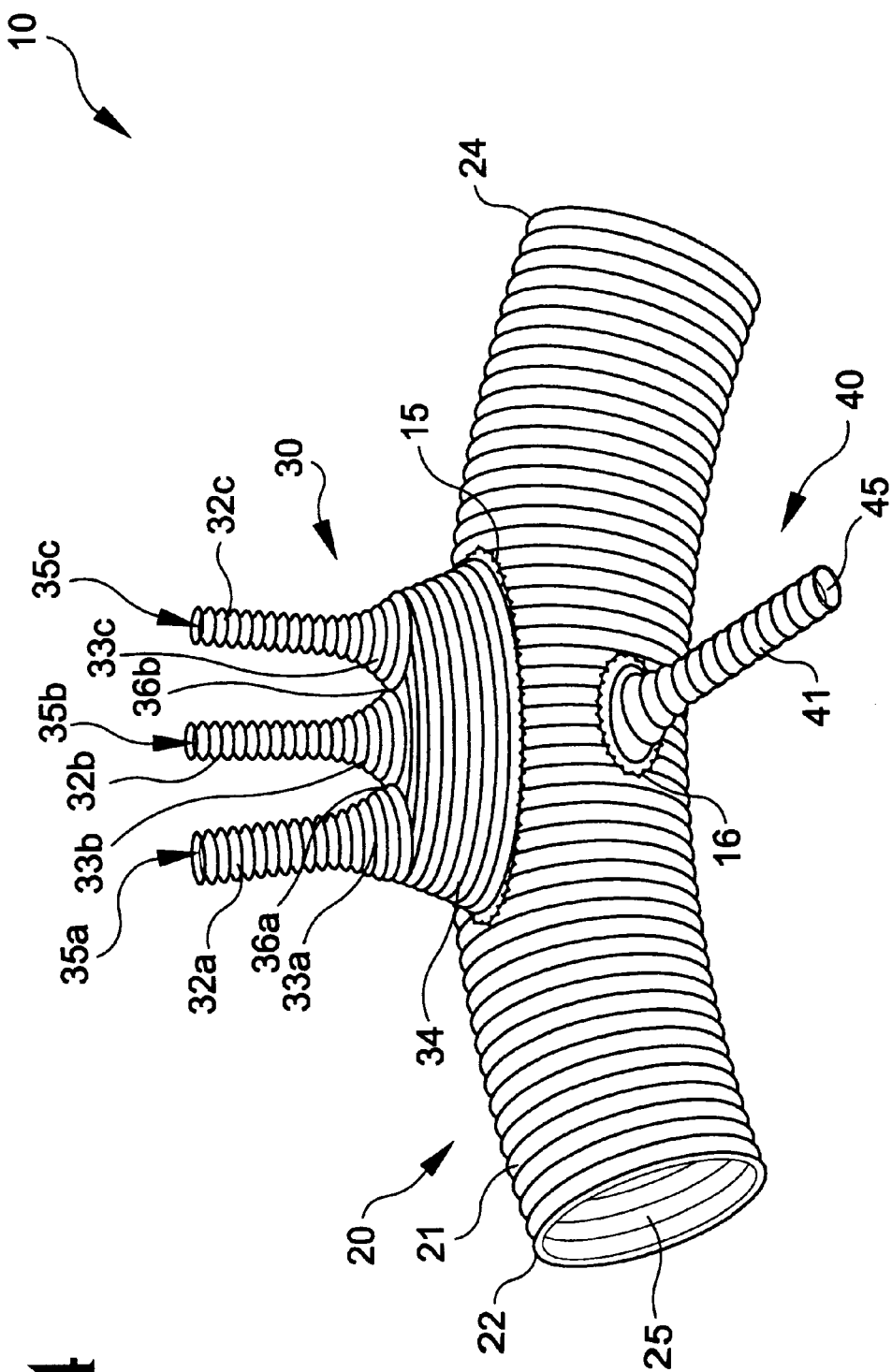
FIG. 4 is a perspective view of an aortic arch graft of the present invention in an alternate embodiment.
Figure 6:
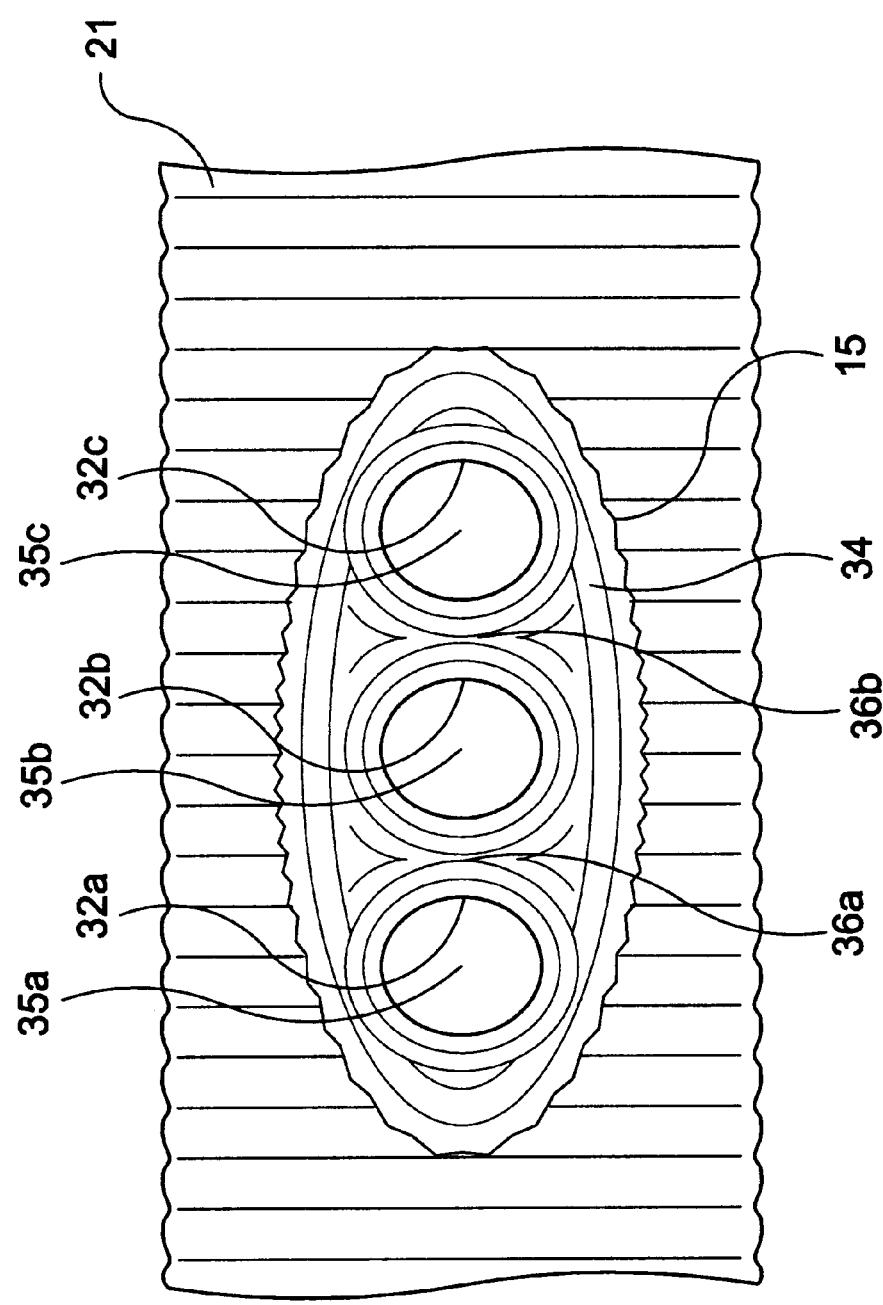
FIG. 6 is a partial cutaway view of a portion of an aortic graft constructed according to the present invention depicting an internal portion of the main wall at the flared transition to the tubular branch.
Figure 7:
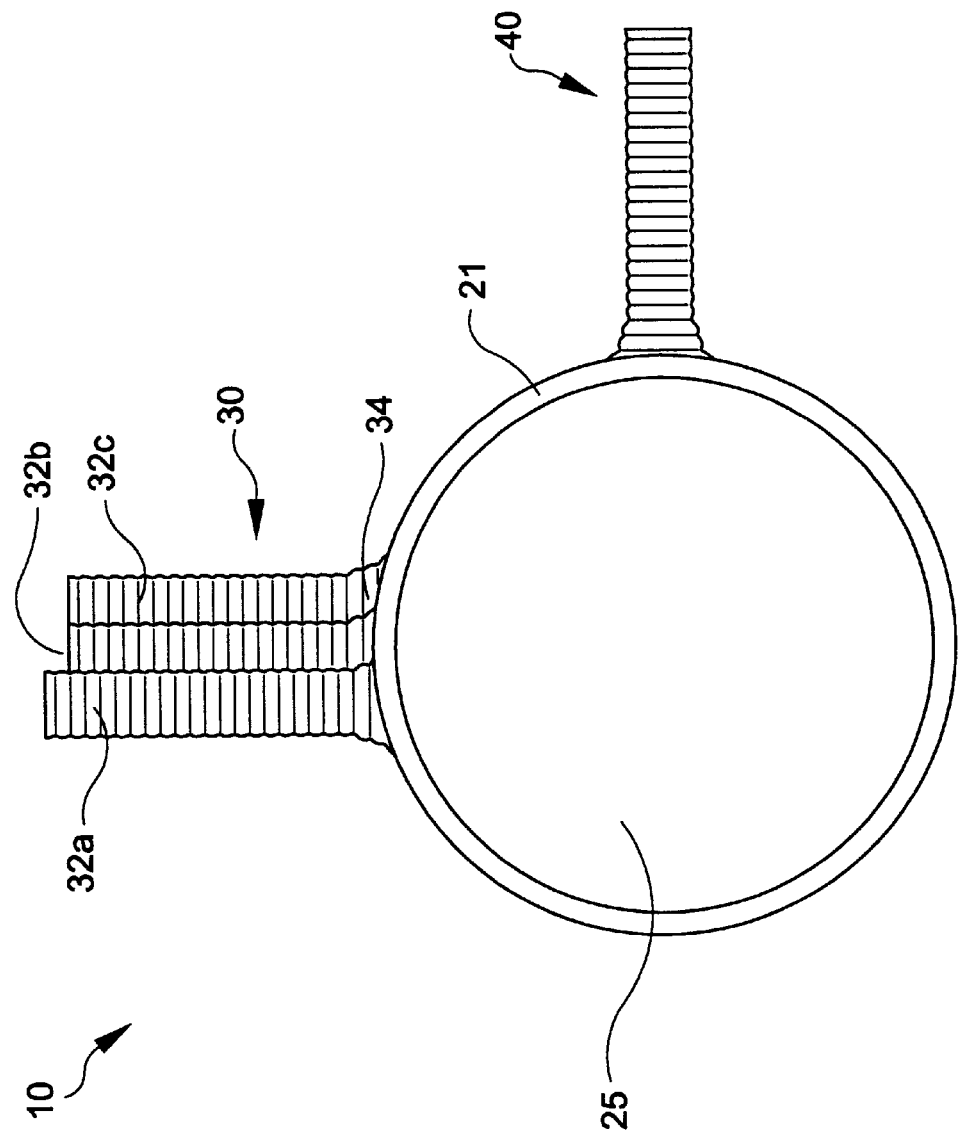
FIG. 7 is an end view of the aortic graft depicted in FIG. 4.

With reference to FIGS. 3, 4, 6 and 7, tubular branch 30 may include a plurality of elongate tubular extents, as best depicted in FIG. 3, which shows branch 30 including three distinct elongate tubular extents 32a, 32b and 32c. Elongate tubular extents 32a, 32b and 32c are preferably equally spaced along an axis with respect to tubular main portion 20. Alternatively, elongate tubular extents 32a, 32b and 32c may be axially spaced and circumferentially offset with respect to tubular main wall 21 of tubular main portion 20, as best depicted in FIGS. 4 and 7.

Prosthesis 10 including a plurality of elongate tubular extents 32a, 32b and 32c is particularly useful as an aortic arch vascular graft. In such an embodiment, each tubular extent 32a, 32b and 32c includes a flared portion 33a, 33b and 33c which is adjacent and contiguous with flared tubular extent 34 and includes junctures 36a and 36b between tubular extents 32a, 32b and 32c. As such, flared tubular extent 34 is contiguous with elongate tubular extents 32a, 32b and 32c.

Elongate tubular extents 32a, 32b and 32c may be of the same length as shown in FIG. 3, or may be of different lengths independently, as shown in FIG. 4.

Each of elongate tubular extents 32a, 32b and 32c includes a generally constant internal diameter along the length thereof, and include branch lumens 35a, 35b and 35c, respectively, extending therethrough. Elongate tubular extents 32a, 32b and 32c may be of the same internal diameter, or may be of different internal diameters independent of one another, as shown in FIG. 4. For example, elongate tubular extents 32a, 32b and 32c may all have the same constant internal diameter of approximately 8 millimeters. Alternatively, elongate tubular extents 32a, 32b and 32c may each have different internal diameters, for example elongate tubular extent 32a may have an internal diameter of approximately 10 millimeters, while elongate tubular extents 32b and 32c may have an internal diameter of approximately 8 millimeters.

In such preferred embodiments where tubular branch 30 includes a plurality of elongate tubular extents 32a, 32b and 32c, the internal diameter of flared tubular extent 34 gradually changes in a similar manner as with the embodiment shown in FIG. 2 in that it increases or flares along the length of flared tubular extent 34.

Flared tubular extent 34 of tubular branch 30 is secured to tubular main wall 21 of tubular main portion 20 along a portion thereof, for example, by sutures 15. As such, a path of fluid communication between main lumen 25 of tubular main portion 20 and branch lumen 35 of tubular branch 30 is established, thereby providing a passageway for blood flow therethrough. Since flared tubular extent 34 incorporates a gradual change in the diameter of tubular branch 32, a smooth and unobstructed path for blood flow is accomplished at the transition to elongate tubular branch 32. The gradual change in diameter with flared tubular extent 34 provides for a smooth transition from main lumen 25 of tubular main portion 20 to branch lumen 35 of tubular branch 30, as opposed to the sharp transition encountered with prior art end-to-side vascular prostheses, as depicted in FIG. 1 and discussed above. Furthermore, in embodiments incorporating a plurality of elongate tubular extents 32a, 32b and 32c including branch lumens 35a, 35b and 35c, respectively, extending therethrough, branch lumens 35a, 35b and 35c converge and contiguously join with flared tubular extent 34 at junctures 36a and 36b. As such, a path of fluid communication exists between branch lumen 35 within flared tubular extent 34 and each of branch lumens 35a, 35b and 35c within elongate tubular extents 32a, 32b and 32c. Thus, with flared tubular extent 34 of tubular branch 30 being secured to tubular main wall 21 of tubular main portion 20 through sutures 15, a smooth and obstructed path of fluid communication between main lumen 25 and each of branch lumens 35a, 35b and 35c is established through branch lumen 35 within flared tubular extent 34.

Figure 5:
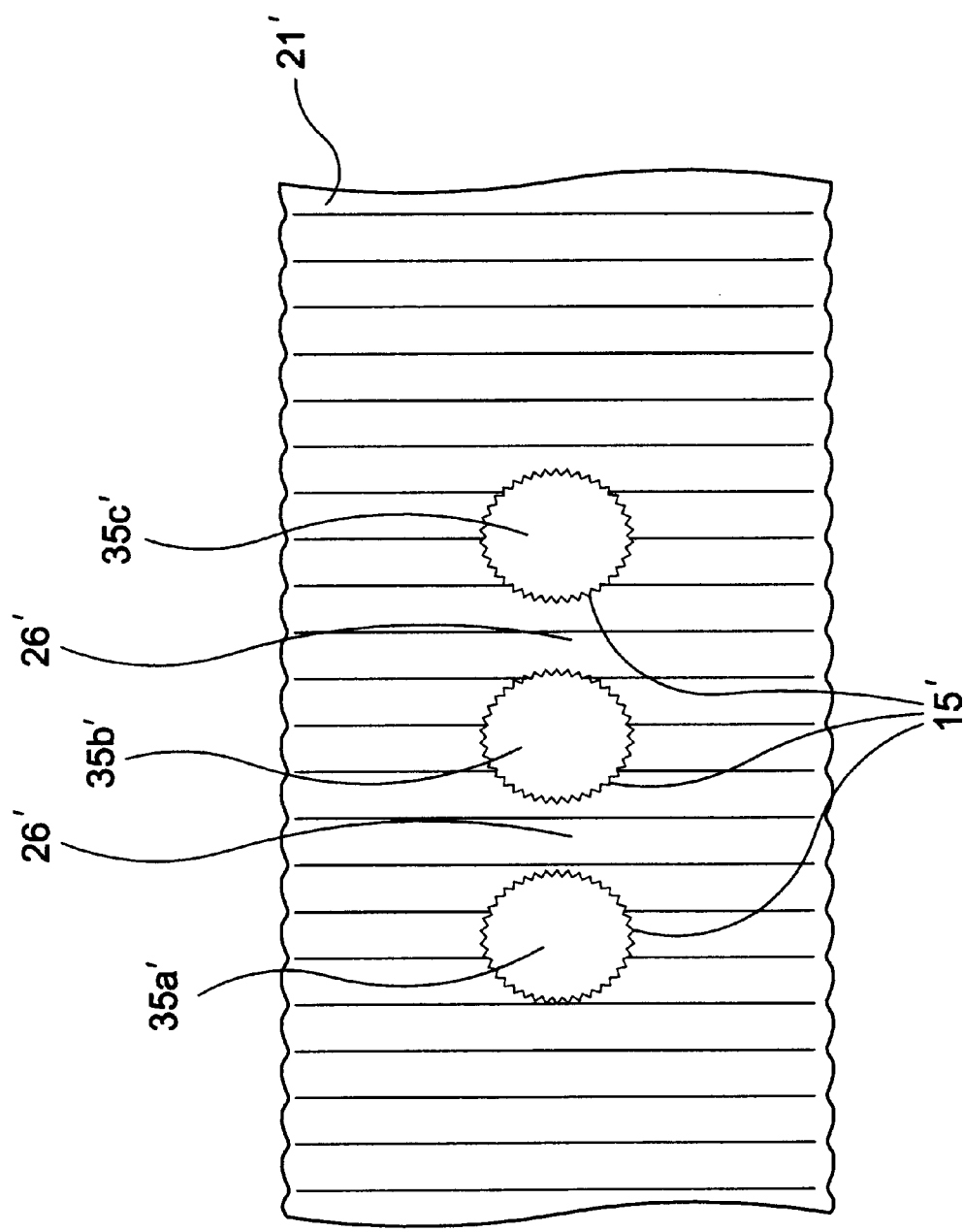
FIG. 5 is a partial cutaway view of a portion of an aortic graft constructed according to the prior art depicting an internal portion of the main wall at the transition to the tubular branches.

FIG. 5 depicts a view of the prior art prosthesis 10' as in FIG. 1, showing a cutaway portion of tubular main wall 21' at the location of securement of tubular branches 30a', 30b' and 30c' viewed from within main lumen 25'. Such individual suturing directly at the transition from main lumen 25' to branch lumens 35a', 35b' and 35c' results in undesirable bulking directly at the point of lumen transition, which can lead to thrombosis at the lumen transition. Furthermore, as is clearly evident in FIG. 5, individual suturing of tubular branches 30a', 30b' and 30c' by way of sutures 15' results in wall portions 26' of main tubular wall 21' extending between the areas of securement of tubular branches 30a', 30b' and 30c'. Such wall portions 26' result in a sharp transition from tubular main lumen 25' to branch lumens 35a', 35b' and 35c'. This sharp transition creates turbulence in the path of blood flow between main lumen 25' and branch lumens 35a', 35b' and 35c', which can result in improper blood flow to the branch lumens 35a', 35b' and 35c'.

FIG. 6 depicts a cutaway portion of prosthesis 10 according to the present invention in a similar manner of FIG. 5, showing tubular main wall 21 at the location of securement of tubular branch 30, viewed from within main lumen 25. Sutures 15 are provided at a location spaced from the transition between main lumen 25 of tubular main portion 20 and branch lumens 35a, 35b and 35c of tubular branch 30. As such, prosthesis 10 does not include any suturing directly at the transition between main lumen 25 and branch lumens 35a, 35b and 35c, in that such lumen transition is accomplished gradually over the length of flared tubular extent 34. Further, flared portions 33a, 33b and 33c of each tubular branch 32a, 32b and 32c together with junctures 36a and 36b therebetween establish a gradual transition region for the path of blood flow between main lumen 25 and branch lumens 35a, 35b and 35c. Thus, undesirable thrombosis at the lumen transition is reduced as compared with prior art grafts, in that prosthesis 10 of the present invention does not incorporate a sharp transition from one lumen to another and does not include any sutures directly at the transition.

Prosthesis 10 may further include an elongate tubular port 40 extending laterally from tubular main wall 21 of tubular main portion 20. Tubular port 40 includes tubular port wall 41 which defines port lumen 45 extending therethrough. Tubular port 40 is secured to tubular main wall 21 of tubular main portion 20, for example by way of port sutures 16. As such, port lumen 45 is in fluid communication with main lumen 25 of tubular main portion 20.

Tubular port 40 is provided as a procedural aid for use during surgical implantation procedures. For example, oftentimes it is desirable to access main lumen 25 of prosthesis 10 during a surgical procedure from outside of the body. Tubular port 40 provides a means for such access. Tubular port 40 is not meant for anastomosis to any part of the body, but is provided for temporary use during a surgical procedure. After completion of an implant procedure, tubular port 40 is preferably ligated and tied off, for example by way of sutures, to provide a completely closed main lumen 25.

Preferably, tubular port 40 extends from tubular main wall 21 at a location remote from tubular branch 30. Most preferably, tubular port 40 extends substantially perpendicularly from tubular main wall 21 at a 90° angle with respect to laterally extending tubular branch 30, as best depicted in FIG. 7.

Prosthesis 10 is preferably capable of maintaining a blood-tight atmosphere at the time of implantation. In order to control the porosity of prosthesis 10, a natural or synthetic sealant may be incorporated into the textile structure, as is known in the art. For example, collagen may be incorporated into the textile structure of prosthesis 10 to act as a sealant. Such collagen is typically resorbed by the body over time, and is replaced with native tissue, which further serves to anchor prosthesis 10 in place within the body.

Having described the prosthesis of the present invention, its construction and manufacture will now be discussed. As noted, the prosthesis of the present invention is constructed of textile material, such as a woven, knitted or braided material. Such textile materials are particularly useful in vascular graft applications, in that the textile pattern of the material can be constructed to be very pliable and capable of permitting sufficient ingrowth of surrounding tissue, while also being capable of maintaining a fluid-tight, i.e., blood-tight wall structure.

The textile prosthesis of the present invention is preferably a woven material, and can be woven using any known weave pattern, including simple weaves, basket weaves, twill weaves, velour weaves and the like, and is most preferably woven using a flat plain tubular weave pattern, preferably with about 100–200 warp yarns per inch per layer and about 70–120 fill yarns per inch per layer, more preferably with about 170–190 warp yarns per inch per layer and about 86–90 fill yarns per inch per layer. The wall thickness of the graft may be any conventional useful thickness, but is preferably no greater than about 1.0 mm, with the most preferable wall thickness being from about 0.10 mm to about 0.75 mm.

Any type of textile product can be used as the yarns or fibers of the present invention. Of particular usefulness are synthetic materials such a thermoplastic polymers. Thermoplastic yarns suitable for use in the prostheses of the present invention include, but are not limited to, polyesters, polypropylenes, polyethylenes, polyurethanes, polytetrafluoroethylenes, and mixtures thereof. The yarns may be of the monofilament, multifilament, or spun type.

The yarns used in forming the grafts of the present invention may be flat, twisted or textured, and may have high, low or moderate shrinkage properties. Additionally, the yarn type and yarn denier can be selected to meet specific properties for the prosthesis, such as porosity, flexibility and compliance. The yarn denier represents the linear density of the yarn (number of grams mass divided by 9,000 meters of length). Thus, a yarn with a small denier would correspond to a very fine yarn whereas a yarn with a larger denier, e.g., 1000, would correspond to a heavy yarn. The yarns used in the prosthesis of the present invention preferably have a denier from about 20 to about 1000, more preferably from about 40 to about 300. Preferably, the warp and fill yarns are polyester, and most preferably the warp and fill yarns are one ply, 50 denier, 48 filament flat polyester.

In preferred embodiments of the present application, prosthesis 10, and in particular tubular main portion 20 and tubular branch 30 are independently constructed of woven textile material. Woven tubular textile products are particularly useful in manufacturing vascular graft products in that a variety of unique shapes and sizes can now be accomplished. For example, in co-pending and co-assigned U.S. Pat. No. 5,800,514, the disclosure of which is incorporated herein by reference, unique tubular woven textile products such as vascular grafts are seamless woven into a variety of shapes and sizes to manufacture blood-tight conduits. In particular, seamless, tapered, blood-tight tubular-woven textile grafts are disclosed, including bifurcated and trifurcated structures which are substantially blood-tight at the juncture between the bi- and trifurcations, and therefore do not require any additional stitching or suturing to maintain a blood-tight wall.

More particularly, it is possible to accomplish disengaging and/or engaging of selected warp yarns to create gradual changes with size, shape or configuration of the graft during weaving of the graft. Such disengaging and/or engaging of the warp yarns must be accomplished in a gradual transition in order to prevent holes or voids between the contiguous sections of the woven graft. It is known that a delicate balance exists between porosity of the graft for proper ingrowth and the need in many applications for fluid-tight walls. It has been determined that a void greater than the diameter of about three warp yarns results in a graft with a porosity which is unacceptable as a fluid-tight conduit and may be incapable of sufficiently maintaining blood pressure therein. Thus, the transition from a graft section of one diameter to a graft section of another diameter, as in the transition from elongate tubular extents 32a, 32b and 32c to flared tubular extent 34, must be accomplished in fluid-tight applications without creating such voids between the contiguous weave sections which are generally greater than the diameter of three warp yarns.

As noted, transition from one diameter to another diameter can be accomplished by gradually engaging and/or disengaging selected warp yarns from the weave pattern. Such a transition can be effectively accomplished by engaging or disengaging a maximum of three warp yarns per four successive machine picks for a given weave pattern on each edge of the graft, as is discussed in more detail in U.S. application Ser. No. 08/653,028, incorporated herein by reference.

Alternatively, transition from one diameter to another diameter can be accomplished in the fabric by a post-manufacturing technique, such as heat-shaping, shrinkfitting, molding, and the like. In such techniques, the tubular branch 30 is constructed of textile material, for example, by weaving, knitting or braiding. Tubular branch 30 may then be fitted onto a mandrel in a desired shape, such as a flared shape, and may be heat-shrunk to set the fibers of the fabric into the desired flared shape of the mandrel. Upon removal from the mandrel, tubular branch 30 is set to the desired flared shape.

Such unique textile structures are particularly useful as tubular branch 30 in the prosthesis of the present invention. For example, a trifurcated tubular structure can be manufactured in a seamless, tubular-woven form, to create a substantially fluid-tight structure. Such structure can then be secured to a separate tubular graft structure in the form of tubular main portion 20 at tubular main wall 21. Thus, prosthesis 10 is produced which incorporates a gradual transitional change in diameter from main tubular lumen 25 to branch lumens 35a, 35b and 35c, which transition is seamless along the length thereof and does not require additional stitching to maintain a fluid-tight construction.

Various other modifications to the foregoing disclosed embodiments will now be evident to those skilled in the art. Thus, the particularly described preferred embodiments are intended to be illustrative and not limited thereto. The true scope of the invention is set forth in the following claims.

What is claimed is:

1. An implantable textile prosthesis comprising:
   a first woven section comprising an elongate tubular main wall defining a fluid passageway therethrough; and
   a second woven section comprising a tubular branch wall defining a fluid passageway therethrough, said tubular branch wall including an elongate tubular extent and an asymptotically flared tubular extent asymptotic with respect to said tubular branch wall, said flared tubular extent being contiguous with said elongate tubular extent, said flared tubular extent including a weaving pattern having a plurality of warp yarns and fill yarns and incorporating a gradual change in the number of warp yarns with respect to said fill yarns to provide a seamless and substantially fluid-tight transition region along said flared tubular extent;
   said second woven section being secured to said first woven section to provide said tubular branch wall extending laterally from said tubular main wall to establish fluid communication between said tubular main wall and said tubular branch wall.

2. An implantable textile prosthesis comprising:
   a first woven section comprising an arched elongate tubular main wall defining a fluid passageway therethrough; and
   a second woven section comprising a flared tubular extent and a plurality of elongate tubular extents, said flared tubular extent being contiguous with said plurality of elongate tubular extents, said flared tubular extent including a weaving pattern having a plurality of warp yarns and fill yarns and incorporating a gradual change in the number of warp yarns with respect to said fill yarns to provide a seamless and substantially fluid-tight transition along said flared tubular extent;
   said second woven section being sutured to said first woven section to provide said a plurality of elongate tubular extents extending laterally from said tubular main wall to establish fluid communication between said tubular main wall and said a plurality of elongate tubular extents through said flared tubular extent.

3. An implantable textile prosthesis comprising:
   an elongate tubular main wall defining a fluid passageway therethrough; and
   a discrete tubular branch wall constructed independently from said tubular main wall and extending laterally from and secured to said tubular main wall and defining a fluid passageway therethrough, said tubular branch wall including a flared tubular extent and a plurality of elongate tubular extents contiguous with said flared tubular extent, said flared tubular extent being secured to said tubular main wall to establish fluid communication between said tubular main wall and said tubular branch wall, said flared tubular extent incorporating a gradual increase in diameter with respect to said plurality of elongate tubular extents to provide a seamless and substantially fluid-tight transition region between said tubular main wall and said tubular branch wall along said flared tubular extent.

4. A prosthesis as in claim 1, wherein said flared tubular extent includes a textile pattern having a plurality of warp yarns and fill yarns and incorporating a gradual change in the number of warp yarns with respect to said fill yarns.

5. A prosthesis as in claim 4, wherein said gradual change in the number of warp yarns in said textile pattern is defined by a change of no more than 3 of said warp yarns for every 2 of said fill yarns to create a substantially fluid tight transition.

6. A prosthesis as in claim 1, wherein said tubular main wall and said tubular branch wall are constructed of a textile material selected from the group consisting of woven material, knitted material, braided material, and mixtures thereof.

7. A prosthesis as in claim 1, wherein said tubular main wall and said tubular branch wall are constructed of material selected from the group consisting of polyester, polypropylene, polyethylene, polyurethane, polytetrafluoroethylene and mixtures thereof.

8. A prosthesis as in claim 1, wherein said tubular branch wall extends substantially perpendicular from said tubular main wall.

9. A prosthesis as in claim 1, wherein said tubular main wall is arched.

10. A prosthesis as in claim 1, wherein said tubular branch wall is sutured to said tubular main wall at said flared transition at a location spaced from said seamless, fluid-tight transition.

11. A prosthesis as in claim 1, wherein said plurality of elongate tubular extents include a flared portion.

12. A prosthesis as in claim 1, wherein said tubular branch wall includes first, second and third elongate tubular extents contiguous with said flared tubular extent.

13. A prosthesis as in claim 12, wherein said first, second and third elongate tubular extents are spaced along an axis with respect to said tubular main wall.

14. A prosthesis as in claim 13, wherein said first, second and third elongate tubular extents are circumferentially offset with respect to said tubular main wall.

15. A prosthesis as in claim 1, wherein said plurality of elongate tubular extents have substantially the same diameters.

16. A prosthesis as in claim 1, wherein said plurality of elongate tubular extents have different diameters with respect to each other.

17. A prosthesis as in claim 1, wherein said plurality of elongate tubular extents have substantially the same lengths.

18. A prosthesis as in claim 1, wherein said plurality of elongate tubular extents have different lengths with respect to each other.

19. A prosthesis as in claim 1, further including an elongate tubular port extending laterally from said tubular main wall at a location remote from said tubular branch wall.

* * * * *